(12) United States Patent
Chan et al.

(10) Patent No.: US 8,518,425 B2
(45) Date of Patent: Aug. 27, 2013

(54) ANTIPERSPIRANT COMPOSITIONS

(75) Inventors: Catrin Sian Chan, Leeds (GB); Martin Peter Cropper, Bebington (GB); Kevin Ronald Franklin, Bebington (GB); Simon Anthony Johnson, Bebington (GB); Robert McKeown, Bebington (GB)

(73) Assignee: Conopco Inc., Englewood Cliffs, NJ (US)

( * ) Notice: Subject to any disclaimer, the term of this patent is extended or adjusted under 35 U.S.C. 154(b) by 403 days.

(21) Appl. No.: 12/605,555

(22) Filed: Oct. 26, 2009

(65) Prior Publication Data

US 2010/0104611 A1    Apr. 29, 2010

(30) Foreign Application Priority Data

Oct. 27, 2008   (EP) .................................... 08167667

(51) Int. Cl.
*A61K 8/02* (2006.01)
*A61K 8/00* (2006.01)
*A61K 9/00* (2006.01)

(52) U.S. Cl.
USPC ............................... 424/401; 424/65; 424/47

(58) Field of Classification Search
None
See application file for complete search history.

(56) References Cited

U.S. PATENT DOCUMENTS

| | | | | |
|---|---|---|---|---|
| 5,043,161 | A | 8/1991 | Scarpelli et al. | 424/401 |
| 5,176,903 | A | 1/1993 | Goldberg et al. | 424/66 |
| 6,083,492 | A * | 7/2000 | Modi | 424/65 |
| 6,171,581 | B1 | 1/2001 | Joshi et al. | 424/65 |
| 2003/0232025 | A1 | 12/2003 | Colwell et al. | 424/65 |
| 2007/0036738 | A1 * | 2/2007 | Fletcher et al. | 424/65 |
| 2009/0047226 | A1 | 2/2009 | Teckenbrock et al. | 424/59 |

FOREIGN PATENT DOCUMENTS

| | | |
|---|---|---|
| EP | 0 201 134 | 11/1986 |
| EP | 0 303 461 * | 2/1989 |
| EP | 0303461 * | 2/1989 |
| EP | 0 385 534 | 9/1990 |
| EP | 0 480 520 | 4/1992 |
| EP | 0 519 531 * | 12/1992 |
| EP | 0519531 * | 12/1992 |
| EP | 1 533 364 | 5/2005 |
| EP | 1 072 259 | 6/2006 |
| EP | 1 797 946 | 6/2007 |
| FR | 2 839 658 | 11/2003 |
| WO | 2005/087181 | 9/2005 |
| WO | 2006/056096 | 6/2006 |
| WO | WO2006/056096 * | 6/2006 |
| WO | WO 2006/056096 * | 6/2006 |
| WO | 2006/0825536 | 8/2006 |
| WO | 2007/124889 | 11/2007 |
| WO | 2008/144079 | 11/2008 |

OTHER PUBLICATIONS

European Search Report in European Application No. 08 16 7667, Mar. 18, 2009.
European Search Report in European Application No. 08 16 7668, Mar. 13, 2009.
European Search Report in European Application No. 08 16 7669, Mar. 18, 2009.
Abstract of FR 2 839 658—published Nov. 21, 2003.
Co-pending Application: Applicant: Cropper et al., U.S. Appl. No. 12/605,570, filed Oct. 25, 2009.
Co-pending Application: Applicant: Chan et al., U.S. Appl. No. 12/605,598, filed Oct. 25, 2009.

* cited by examiner

*Primary Examiner* — Daniel Sullivan
*Assistant Examiner* — Melissa Javier
(74) *Attorney, Agent, or Firm* — Karen E. Klumas

(57) ABSTRACT

Anhydrous antiperspirant compositions comprising particulate antiperspirant active; capsules comprising a shear-sensitive shell which encapsulates perfume; and a carrier for the particulate antiperspirant active and capsules; wherein the capsules have a shell of cross-linked gelatin coacervate having a thickness of from 0.25 to 9 μm and providing from 10 to 40% by weight of the capsules, a volume average particle diameter of from 25 to 70 μm, a ratio of shell thickness to the average particle diameter in the range of from 1:5 to 1:120, and a Hysitron hardness in the range of from 1.5 MPa to 50 MPa.

19 Claims, No Drawings

ANTIPERSPIRANT COMPOSITIONS

The present invention relates to antiperspirant compositions and more particularly to anhydrous antiperspirant compositions comprising encapsulated fragrance.

Antiperspirant compositions comprising encapsulated fragrance are known in the art. Most of these compositions comprise moisture-sensitive encapsulates, such as those based on gum arabic or gum acacia, starch or certain modified starches, rather than the shear-sensitive encapsulates employed in the present invention.

WO2006/056096 (Givaudan SA) discloses shear-sensitive encapsulates, largely focussing on their use in fabric conditioner compositions. Amongst the fabric conditioner examples, there is also disclosed as Example 9 an anhydrous antiperspirant composition, comprising gelatin capsules containing 20% fragrance. This prior art is silent concerning antiperspirant compositions comprising capsules having higher levels of encapsulated fragrance and lower levels of encapsulating shell.

The present invention is concerned with overcoming the problems encountered in providing antiperspirant compositions that allow triggered release of fragrance. The twin benefits of encapsulate stability during formulation and release of the encapsulated fragrance when desired are very difficult to achieve and require a precise selection of parameters for the encapsulates employed.

Throughout this specification it should be understood that the terms "perfume" and "fragrance" may be used interchangeably and have essentially the same meaning. Likewise, when the term "encapsulate" is used as a noun, it has essentially the same meaning as the word "capsule".

According to a first aspect of the present invention, there is provided an anhydrous antiperspirant composition comprising particulate antiperspirant active; capsules comprising a shear-sensitive shell which encapsulates perfume; and a carrier for the particulate antiperspirant active and capsules; wherein the capsules have a shell of cross-linked gelatin coacervate having a thickness of from 0.25 to 9 µm and providing from 10 to 40% by weight of the capsules, a volume average particle diameter of from 25 to 70 µm, a ratio of shell thickness to the average particle diameter in the range of from 1:5 to 1:120, and a Hysitron hardness in the range of from 1.5 MPa to 50 MPa.

According to a second aspect of the present invention there is provided a cosmetic method of reducing perspiration and perfuming the human body comprising the application thereto of a composition according to the first aspect of the present invention.

According to a third aspect of the present invention, there is provided a method of manufacture of a composition according to the first aspect of the present invention.

The selection of encapsulates satisfying the specified parameters according to the present invention can combine manufacturing capability under the conditions for making anhydrous antiperspirant compositions with greater availability of releasable fragrance in the underarm. This is particularly true for anhydrous stick or aerosol compositions for the reasons described herein.

The use of shear-sensitive, rather than water-sensitive encapsulates in the present invention relates to the desired mode of rupture of the encapsulates and subsequent release of fragrance. Water-sensitive encapsulates, such as those made from starch or certain modified starches retain their content until moisture becomes present. When applied the underarm, release of encapsulated perfume from such capsules only happens after sweating has commenced. The present invention concerns a different form of body-induced rupture of the encapsulates. When shear-sensitive encapsulates are applied the underarms, rupture may be achieved by simple movement of the arms against the body, creating shear stresses in the underarm. The consumer may then experience a desirable fragrance release, whilst exercising for example. The fragrance release does not require the consumer to have started sweating, something uncomfortable and disappointing when one has applied a supposedly efficacious antiperspirant composition.

The present invention employs an anhydrous composition, with the antiperspirant active and fragrance capsules typically suspended in a carrier material. Such compositions do not have significant levels of water present which can, in many compositions, act as a lubricant and reduce shear stress upon encapsulates contained therein. The particulate encapsulates in such compositions are "dry", being in an anhydrous composition. Such compositions require careful selection of the encapsulates in order to have stability in manufacture and storage and yet still deliver fragrance when desired.

Anhydrous compositions should be understood to comprise less than 1% by weight of free water. "Free" water excludes water chemically or physically bound to other components of the composition, such as water associated with the particulate antiperspirant active.

A further problem with anhydrous antiperspirant compositions comprising shear-sensitive perfume encapsulates concerns their application to the body. Typical means of application are spraying (e.g. for aerosol compositions) and rubbing (e.g. for stick compositions). Both of these means of application can produce shear stress on the composition, whether on passing through the nozzle of a spray dispenser or on being directly rubbed against the body. It is not desirable for the majority of the encapsulated fragrance to be released at this stage. Hence, the perfume encapsulates employed in such compositions must have carefully selected properties in order to avoid premature rupture.

A particularly important parameter of the encapsulates used in the present invention is their level of shell material. This is relatively low, being only from 10 to 40% by weight. This enhances the capsules ability to be ruptured. With higher levels of shell material and consequential lower levels of encapsulated material, the capsules can become too hard and not rupture sufficiently for significant fragrance to be released under the desired stimulus.

The present invention may be employed in the form of a spray composition, in particular, an aerosol spray composition. In such use, it is important that the capsules are sufficiently robust to not only to survive the manufacturing process, but also to survive the stress of being forced through the narrow spray outlet of a conventional spray dispenser and yet still be shear-sensitive on the skin.

The present invention relates to the incorporation into anhydrous antiperspirant compositions of shear-sensitive perfume capsules, the term capsules herein including microcapsules. Shear-sensitive herein contemplates that the capsule is capable of releasing its perfume contents as a result of normal shear stresses encountered in the underarm region, including shear against clothing. The shear-sensitive capsules may alternatively be termed "friction-sensitive" or "pressure-sensitive".

The encapsulating material or shell for the shear-sensitive capsules herein is a cross-linked gelatine coacervate. One process suitable for forming such capsules is often called complex coacervation, and is described in U.S. Pat. No. 6,045,835. In such a process, an aqueous solution of a cationic polymer, commonly gelatin or a closely related cationic polymer, is formed at an elevated temperature that is high enough to dissolve the gelatin, commonly at least 40° and in many instances it is unnecessary to exceed 70° C. A range of 40 to 60° C. is very convenient. The solution is typically dilute, often falling in the range of from 1 to 10% w/w and particularly from 2 to 5% w/w. Either before or after dissolution of the gelatin, an oil-in-water emulsion is formed by the introduction of a perfume oil, optionally together with a diluent oil if desired.

A polyanion or like negatively charged polymer is introduced and the composition diluted until a pH is attained of below the isoelectric point of the system, such as below pH5, and particular from pH3.5 to pH 4.5, whereupon a complex coacervate forms around the dispersed perfume oil droplets. The polyanion commonly comprises gum arabic or a charged carboxymethyl cellulose derivative, such an alkali metal salt, of which sodium is the most commonly mentioned example.

The resultant shell is subsequently cross linked, with a short chain aliphatic dialdehyde, for example a $C_4$ to $C_6$ dialdehyde, including in particular glutaraldehyde. The cross linking step is commonly conducted at a temperature of below ambient such as from 5 to 15° C., and particularly in the region of 10° C. Representative weights and proportions of the reactants and of suitable operating conditions are shown in Examples 1, 2 or 3 of the aforementioned U.S. Pat. No. 6,045,835. The skilled man by suitable selection of the parameters within the general process outlined therein is well capable of producing capsules having a volume average particle size in the range of from 30 to 100 μm, particularly up to 75 μm and especially 40 to 60 μm.

A second encapsulation method that is likewise suitable for forming encapsulated perfumes in which the shell comprises cross-linked coacervated gelatin comprises variations of the above process, as contemplated in WO2006/056096. In such variations, microcapsules comprising a blank hydrogel shell are first formed in a dry state and brought into contact with an aqueous or aqueous/alcoholic mixture of a fragrance compound, commonly diluted with a diluent oil. The fragrance compound is transported through the hydrogel shell by aqueous diffusion and is retained inside. The resultant fragrance-containing microcapsules are then dried to a powder, which for practical purposes is anhydrous. Although selection of the ratio of fragrance oil to diluent oil is at the discretion of the producer, and may be varied over a wide range, the ratio is often selected in the range of from 1:2 to 1:1, and particularly 3:4 to 1:1, for fragrance to diluent oils.

The proportion of shell material to core perfume oil is crucial, and is attainable by appropriately varying the proportions of the ingredients in the emulsion. It is required for the shell material to constitute from 10 to 40% by weight and especially from 12 to 25% by weight of the capsules. By varying the proportions of shell and core, the physical strength of the shell can be varied (for capsules of the same volume average particle size). Accordingly, capsules having the desired combination of characteristics can be selected.

In some preferred embodiments of the present invention, the fragrance oil constitutes from 70 to 85% by weight of the encapsulates and in such embodiments, the balance is provided by the shell.

In other preferred embodiments, the fragrance oil is present together with an oil diluent, for example providing from 25 to 75% by weight of the oil mixture held within the shell, and especially from 40 to 60% by weight. Desirably in such embodiments, the shell constitutes from 12 to 25% by weight of the encapsulates. In certain of such preferred embodiments, the fragrance constitutes from 35 to 50% by weight of the encapsulates, and is complemented by 35 to 50% by weight of diluent oil. If desired, in yet other embodiments, the composition contains some of the encapsulates that contain diluent oil and others that do not, the weight ratio of the two sets of encapsulates being selected in the range of from 25:1 to 1:25 at the discretion of the producer.

It is preferred for the volume average particle diameter (size) of the capsules to be at least 40 μm and in many desirable embodiments is up to 60 μm in diameter.

Herein, unless otherwise indicated, the volume average particle diameter of the encapsulates (D[4,3]) is that obtainable using a Malvern Mastersizer, the encapsulates being dispersed in cyclopentasiloxane (DC245) using a dispersion module mixer speed of 2100 rpm. Calculations are made using the General Purpose model, assuming a spherical particle shape and at Normal calculation sensitivity.

The shell thickness of the microcapsules tends to increase as the particle size increases and is in the range of from 0.25 to 9 μm. Preferably at least 90% by volume of the capsules have shells of up to 2.5 μm thickness. Desirably, at least 95% by volume of the capsules have a shell thickness of at least 0.25 μm. The average shell thickness of microcapsules desirably employed herein is up to 1.5 μm. The same or other suitable capsules have an average shell thickness of at least 0.4 μm. For capsules of diameter up to 40 μm, the shell thickness is often below 0.75 μm, such as from 0.25 to less than 0.75 μm whereas for particle of at least 40 μm the shell thickness is often from 0.6 to 2.5 μm.

The shell thickness can be measured by solidifying a dispersion of the capsules in a translucent oil, cutting a thin slice of the solid mass and using a scanning electron microscope to obtain an image of cut-through individual capsules, thereby revealing the inner and outer outline of its annular shell and hence its thickness.

The fragrance-containing capsules for incorporation in the anhydrous antiperspirant compositions are commonly selected having a ratio of volume average diameter to average shell thickness in the range of from 10:1 to 100:1 and in many desirable such capsules in the range of from 30:1 or 40:1 to 80:1.

By virtue of the particle size and the shell thickness of the capsules, the average % volume of the core containing the fragrance oils and any diluent oil, if present, often falls within the range of from 50 to 90%, and in many embodiments from 70 to 87.5%.

The hardness of the capsules, as measured in a Hysitron Tribo-indenter, is an important characteristic that enables them to be incorporated effectively in anhydrous formulations, retaining the capability of being sheared by frictional contact between skin and skin or clothing. The hardness is desirably in the range of from 0.5 to 50 MPa and especially from 2.5 or 5 up to 25 MPa, and in many embodiments is up to 10 MPa. In certain preferred embodiments, the hardness is in the range of from 3.5 to 5.5 MPa.

A further parameter of interest in relation to the capsules in the instant invention, and particularly their capability to be sheared by friction in the compositions and process of the instant invention, is their "Apparent Reduced Elastic Modulus" (Er). Desirably, Er falls within the range of from 20 to 35 MPa, and in many convenient embodiments, in the range of from 22 to 30 MPa.

Measurements of Hysitron hardness (H) and Apparent Reduced Elastic Modulus (Er) are made in the following manner.

Having appropriately mounted a given capsule, the head of the Tribo-indenter, fitted with a Berkovich tip (a three-sided pyramid) compresses the capsule. The instrument is programmed to perform an indent by compressing the sample with an initial contact force of 75 μN, for 10 seconds, followed by a position hold stage for 1 second and a decompression stage for 10 seconds. The instrument achieves a very small load (typically around 15-30 μN). The Hysitron Hardness (MPa) and Apparent Reduced Elastic Modulus (also in MPa) are calculated from the relaxation stage of the force deflection data using the following equations.

$$H = \frac{W}{A}$$

W=Compressive force
A=Contact Area ($A \approx 24.56 h_c^2$)

$$Er = \frac{\sqrt{\pi}}{2\gamma} \frac{S}{\sqrt{A}}$$

S=Contact Stiffness ($dW/dh_t$)
$h_{554}$ =Total Penetration Depth
$\gamma$=1.034

$$h_c = h_i - \kappa \frac{W}{S}$$

K=¾
$h_c$=Contact Depth.

By control of the manufacturing process conditions, the resultant dry capsules having the characteristics specified in the ranges or preferred ranges for particles size and mean diameter described herein can be obtained.

The capsules, by virtue of their manufacture route often contain a small residual water content. It is desirable, for example, as measured by the conventional Karl Fischer method, to select capsules having a residual water content of below 5% by weight and particularly below 4% by weight, such as from 0.5 to 3.5% and particularly from 0.6 to 3% w/w (based on the fragrance-containing capsule). Based on the weight of the shell, said water content of the capsules employed herein often falls in the range of from 1% to 20% w/w. By limiting the proportion of water in the capsule, and particularly in the shell, it is possible to avoid at least partly, and preferably substantially, the formation of grit within the anhydrous formulation, and thereby avoid the negative sensation of grit on underarm skin. Grit occurs typically when particles aggregate to form agglomerates that are not readily fractured into their constituent particles. Accordingly, in regard to aerosol or spray compositions, the avoidance of grit formation has a second benefit of reducing the likelihood of blockage of the spray nozzle.

The shear sensitive encapsulate or mixture of encapsulates can be employed in the antiperspirant compositions in an amount at the discretion of the formulator. Commonly, the amount is at least 0.05%, in many instances at least 0.1% and often at least 0.3% by weight of the composition. Usually, the amount is up to 5%, desirably up to 4% and in many instances is up to 3% by weight of the composition. A convenient range is from 0.5 to 2.5% by weight of the composition. Accordingly, the base compositions before introduction of propellant contain a proportionately higher proportion of the encapsulate.

The perfume oil employable herein in the shear sensitive capsules, and/or other capsules and/or non-encapsulated can be selected as is conventional to attain the desired aesthetic result, and comprises usually a blend of at least 5 components, and often at least 20 components. The components can be synthetic or natural extractions, and, in the case of natural oils or oils produced to mimic natural oils, are often mixtures of individual perfume compounds. The perfume oil can comprise, inter alia, any compound or mixture of any two or more such compounds coded as an odour (2) in the Compilation of Odor and Taste Threshold Values Data edited by F A Fazzalari and published by the American Society for Testing and Materials in 1978.

Often, though not exclusively, the perfume compounds acting as perfume components or ingredients in blends have a ClogP (octanol/water partition coefficient) of at least 0.5 and many a ClogP of at least 1. Many of the perfume components that are employable herein can comprise organic compounds having an odour that is discernible by humans that are selected within the chemical classes of aldehydes, ketones, alcohols, esters, terpenes, nitriles and pyrazines. Mixtures of compounds within classes or from more than one class can be blended together to achieve the desired fragrance effect, employing the skill and expertise of the perfume.

Alternatively or additionally, the fragrance incorporated into the capsules can comprise one or a mixture of perfume essential oils, either mixed with each or and/or with synthetic analogues and/or one or more individual perfume compounds, possibly extracted from blossom, leaves, seeds fruit or other plant material. Oils which are herein contemplated include oils from:

Bergamot, cedar atlas, cedar wood, clove, geranium, guaiacwood, jasmine, lavender, lemongrass, lily of the valley, lime, neroli, musk, orange blossom, patchouli, peach blossom, petotgrain, pimento, rose, rosemary, and thyme.

It will be recognised that since naturally derived oils comprise a blend in themselves of many components, and the perfume oil commonly comprises a blend of a plurality of synthetic or natural perfume compounds, the perfume oil itself in the encapsulate does not exhibit a single boiling point, ClogP or ODT, even though each individual compound present therein does.

If desired, the composition can include one or more perfume ingredients that provide an additional function beyond smelling attractively. This additional function can comprise deodorancy. Various essential oils and perfume ingredients, for example those passing a deodorant value test as described in U.S. Pat. No. 4,278,658 provide deodorancy as well as malodour masking.

In the invention described herein, the carrier in which the capsules (and the antiperspirant active) are suspended may comprise one or more oils, by which is meant liquids that are water-immiscible. Such oils are characterised by being liquid at 20° C. (at 1 atmosphere pressure) and are often selected from silicone oils, hydrocarbon oils, ester oils, ether oils and alcohol oils or a mixture of two or more oils selected from such classes of oils. It is highly desirable that the oil has a boiling point of above 100° C. and preferably above 150° C.

One class of oils that is highly favoured comprises volatile silicone oils, which often contribute from 20% to 95% by weight of a blend of oils, particularly at least 30% and in many convenient blends at least 40% by weight. It is advantageous in the instant invention to employ a blend in which the weight proportion of the volatile silicone oils is up to 80% by weight, and particularly up to 70% by weight. The balance of the oils in the blend is provided by one or more non-volatile silicone oils and/or one or more of the other classes of oils.

Herein, a volatile silicone oil is a liquid polyorgano-siloxane having a measurable vapour pressure at 25° C. of at least 1 Pa, and typically in a range of from 1 or 10 Pa to 2 kPa. Volatile polyorganosiloxanes can be linear or cyclic or mixtures thereof. Preferred cyclic siloxanes, otherwise often referred to as cyclomethicones, include polydimethylsiloxanes and particularly those containing from 3 to 9 silicon atoms, preferably at least 4 and especially at least 5 silicon atoms. Preferred cyclomethicones contain not more than 7 silicon atoms and very preferably up to 6 silicon atoms. Volatile silicone oils herein desirably contain on weight average from 4.5 to 5.9 silicone atoms, and especially at least 4.9.

Preferred linear polyorganosiloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise linear or cyclic siloxanes such as the aforementioned linear or cyclic siloxanes substituted by one or more pendant -O-Si(CH$_3$)$_3$ groups, the resultant compounds desirably containing not more than 7 silicon atoms. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

Highly desirably, the compositions according to the present invention comprise either an ether oil or an ester oil or both, preferably in a proportion of greater than 10% w/w of the composition, and particularly greater than 20% w/w. Although together, they could constitute up to 100% w/w of the carrier oils blend, it is desirable that together they contribute no greater than 60% w/w and in many compositions, they total up to 50% w/w of the blend.

The ester oils can be aliphatic or aromatic. Suitable aliphatic ester oils comprise at least one residue containing from 10 to 26 carbon atoms and a second residue of at least 3 carbon atoms up to 26 carbon atoms. The esters may be mono or diesters, and in the latter be derived from a C$_3$ to C$_8$ diol or di carboxylic acid. Examples of such oils include isopropyl myristate, isopropyl palmitate, myristyl myristate.

It is especially desirable to employ an aromatic ester, including especially benzoate esters. Preferred benzoate esters satisfy the formula Ph-CO—O—R in which R is:—
an aliphatic group containing at least 8 carbons, and particularly from 10 to 20 carbons such as from 12 to 15, including a mixture thereof;
or an aromatic group of formula -A-Y-Ph in which A represents a linear or branched alkylene group containing from 1 to 4 carbons and Y represents an optional oxygen atom or carboxyl group.
Particularly preferably, the aromatic ester comprises C$_{12-15}$ alkyl benzoate.

The ether oil preferably comprises a short chain alkyl ether of a polypropylene glygol (PPG), the alkyl group comprising from C2 to C6, and especially C4 and the PPG moiety comprising from 10 to 20 and particularly 14 to 18 propylene glycol units. An especially preferred ether oil bears the INCI name PPG14-butyl ether.

The ester and ether oils herein are preferably selected to have a boiling point in excess of 100° C. This enables them to be employed with all wax systems for solidifying the oil in the carrier that typically melts at no higher than 95° C., and commonly between 65 and 85° C. For sticks made using small molecule gelling agents, it is preferable to select oils having a boiling point in excess of 150° C., and they, naturally, are suitable in conjunction with wax systems too.

The ester and ether oils can be present in the composition in a weight ratio to each other of from 1:0 to 0:1, and in some embodiments from 10:1 to 1:10.

Indeed, though such oils have a number of other beneficial properties, such as for example, reducing the extent to which the antiperspirant formulation is visible after application on the skin, compositions in which the oil blend contains only a minor as compared with a major proportion of such ether and ester oils tend to exhibit sensory attributes preferred by many consumers. In practice, it is desirable for greater than 5% by weight of the oil blend, especially greater than 10% and especially greater than 15% by weight of the oil blend to be furnished by the ester and ether oils. The combined weight of the two oils is preferably less than 60%, particularly less than 50% and especially less than 40% of the weight of the oil blend.

The carrier oil blend can further comprise one or more other water-immiscible oils that have a melting point of below 20° C. and a boiling point of above 100° C. and preferably above 150° C., including hydrocarbon oils, including preferably non-volatile hydrocarbon oils, non-volatile silicone oils and aliphatic monohydric alcohols.

In the instant invention, non-volatile oils, sometimes referred to as emollient oils, such as non-volatile silicone or/and hydrocarbon oils can desirably be included to alter the sensory attributes of the compositions containing, such as to soften the skin or to assist in masking the visibility of particulate materials deposited on the skin. However, it is desirable to restrict the proportion of such non-volatile oils to less than 30% by weight of the oil blend, and in various compositions according to the instant application, the total proportion of such oils is from 5 to 20% by weight.

Examples of suitable non-volatile hydrocarbon oils include polyisobutene and hydrogenated polydecene. Examples of suitable non-volatile silicone oils include dimethicones and linear alkylarylsiloxanes. The dimethicones typically have an intermediate chain length, such as from 20 to 100 silicon atoms. The alkylarylsiloxanes are particularly those containing from 2 to 4 silicon atoms and at least one phenyl substituent per silicon atom, or at least one diphenylene group. The aliphatic alcohol desirably is a branched chain monohydric alcohol containing from 12 to 40 carbon atoms, and often from 14 to 30 carbon atoms such as isostearyl alcohol.

One further class of ester oils that can constitute a fraction of the ester oils contemplated in the invention compositions comprises natural plant oils, commonly containing glyceride esters and in particular the glyceride triesters of unsaturated C18 aliphatic carboxylic acids, such as linoleic acid, linolenic acid or ricinoleic acid, including isomers such as linolenelaidic acid, trans 7-octadecenoic acid, parinaric acid, pinolenic acid punicic acid, petroselenic acid, columbinic acid and stearidonic acid. Examples of such beneficial natural oils include caster oil, coriander seed oil, impatiens balsimina seed oil, parinarium laurinarium kernel fat, sabastiana brasilinensis seed oil borage seed oil, evening primrose oil, aquilegia vulgaris oil, for and sunflower oil and safflower oil. Such oils can desirably comprise from 1 to 10% by weight of the oil blend.

The weight of fragrance materials is not included herein in calculating the weight of the oil blend, irrespective of whether the fragrance is encapsulated or "free".

The compositions of the invention comprise a particulate antiperspirant active. Such antiperspirant actives are preferably incorporated in an amount of from 0.5-50%, particularly from 5 to 30% and especially from 10% to 26% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al).

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from B K Giulini, from Summit and from Reheis, though with differing particle size distributions. Many aluminium and/or zirconium-containing astringent antiperspirant salts employed herein have metal:chloride mole ratio in the range of 1.3:1 to 1.5:1. Others having a lower metal:chloride mole ratio, such as from 1:1 to 1.25:1 tend to generate lower pHs when applied to skin and thus tend to be more irritating.

The proportion of solid antiperspirant salt in a suspension composition normally includes the weight of any water of hydration and any complexing agent that may also be present in the solid active.

Many particulate antiperspirants employed in the instant invention have a refractive index (RI) of at least 1.49 and not higher than 1.57. Actives which are free from zirconium tend to have an RI of from 1.49 to 1.54, depending on their formula and at least partly on their residual water content. Likewise, actives which contain zirconium tend to have an RI of from 1.52 to 1.57.

The selection of the antiperspirant active material desirably takes into account the type of applicator from which it is dispensed. Thus, in many particularly preferred embodiments in which the composition is dispensed from a contact applicator, for example using a stick, cream (soft solid) or roll-on dispenser, the antiperspirant active comprises an aluminium-zirconium active, such as AZAG. However, in other highly preferred embodiments in which the composition is dispensed as a spray, such as using an aerosol dispenser, the antiperspirant active is highly desirably an aluminium chlorohydrate (ACH) or an activated aluminium chlorohydrate (AACH).

For incorporation of compositions according to the present invention, desirably at least 90%, preferably at least 95% and especially at least 99% by weight of the particles having a diameter in the range of from 0.1 μm up to 100 μm. For incorporation in contact applicators, such as stick, soft solid or roll-on dispensers, the antiperspirant particles usually have an average particle diameter of at least 1 μm and especially below 20 μm. In some highly desirable contact compositions the particles by weight have an average particle size of at least 2 μm and particularly below 10 μm, such as in the range of from 3 to 8 μM.

For incorporation in non-contact applicators and especially in aerosols in which the composition is expelled from the dispenser by a propellant gas, possibly augmented by a mechanical or electromechanical propulsive means, it is especially desirable for less than 5% by weight, particularly less than 1% by weight and advantageously none of the particles to have a diameter of below 10 μl. Preferably for inclusion in aerosol compositions, the particles have a diameter of below 75 μm. In many preferred aerosol compositions, the antiperspirant has an average ($D_{50}$) particle diameter in the range of from 15 to 25 μm. The particle size of the antiperspirant active or mixture of actives can be measured using a Malvern Mastersizer, similarly to measurement of the perfume microcapsules size, as mentioned hereinbefore.

The invention compositions can, if desired, include one or more thickeners or gellants (sometimes called structuring or solidifying agents) to increase the viscosity of or solidify the oil blend in which the particulate materials are suspended as is appropriate for application from respectively roll-on dispensers, soft solid (anhydrous cream) dispensers or stick dispensers. Such thickeners or gellants are selected by the skilled man and enough of them is incorporated to attain the desired viscosity or hardness of the resulting roll-on, lotion or soft solid composition, the actual amount employed taking into account the inherent thickening or gelling capability of the chosen material or combination of materials and their ability to form such a chosen form.

In alternative embodiments, for application from a pressurized aerosol dispenser, the anhydrous composition, deemed to be a base composition, and desirably incorporating a suspension aid, is blended with a propellant.

For application from a roll-on, sufficient thickener is introduced to increase the viscosity of the resultant composition to within the range, typically, of from 1000 to 7000 mPa·s and particularly within 2500 to 5500 mPa·s. Viscosities herein are measured in a Brookfield RVT viscometer equipped with a stirrer TA and Hellipath, rotating at 20 rpm at 25° C.

For use as a soft solid, sufficient thickener is introduced to increase the viscosity of the resultant composition to a hardness of from 0.003 to 0.5 Newton/mm², and commonly from 0.003 or 0.01 up to 0.1 Newton/mm$^2$. Hardness can be measured using a Stable Micro systems TA.XT2i Texture Analyser. A metal sphere, of diameter 9.5 mm, is attached to the underside of its 5 kg load cell, and positioned just above the sample surface. Under control of Expert Exceed™ software, the sphere is indented into the sample at an indentation speed of 0.05 mm/s for a distance of 7 mm and reversed to withdraw the sphere from the sample at the same speed. Data comprising time(s), distance (mm) and force (N) is acquired at a rate of 25 Hz. The hardness H at a penetration of 4.76 mm is calculated using the formula $$H=F/A$$

in which H expressed in N·mm$^{-2}$, F is the load at the same traveled distance in N and A is the projected area of the indentation in mm$^{-2}$.

Stick compositions herein desirably have a hardness as measured in a conventional penetration test of less than 30 mm, preferably less than 20 mm and particularly desirably less than 15 mm. Many have a penetration of from 7 to 13 or 7.5 to 12.5 mm. The conventional penetration test employed herein, utilises a lab plant PNT penetrometer equipped with a Seta wax needle (weight 2.5 grams) which has a cone angle at the point of the needle specified to be 9°10'+/−15'. A sample of the composition with a flat upper surface is used. The needle is lowered onto the surface of the composition and then a penetration hardness measurement is conducted by allowing the needle with its holder to drop under the combined weight of needle and holder of 50 grams for a period of five seconds after which the depth of penetration is noted. Desirably the test is carried out at six points on each sample and the results are averaged.

In stick compositions according to the present invention, it is preferred to include a structurant, usually selected from non-polymeric fibre-forming gellants and waxes, optionally supplemented a particulate silica and/or an oil-soluble polymeric thickener. Structurants are generally employed at a level of from 1.5 to 30% by weight.

Non-polymeric fibre-forming gellants are dissolved in a water-immiscible blend of oils at elevated temperature and on cooling precipitate out to form a network of very thin strands that are typically no more than a few molecules wide. One particularly effective category of such thickeners comprises N-acyl amino acid amides, in particular N-acyl glutamic acid dialkylamides, such as N-lauroyl glutamic acid di n-butylamide and N-ethylhexanoyl glutamic acid di n-butylamide and especially mixtures thereof.

The term "wax" refers to materials that are solid at 30° C.; melt to give a mobile liquid at a temperature above 40° C. and generally below 95° C.; are water-insoluble and remain water-immiscible when heated above their melting point. Examples of waxes include hydrocarbon waxes, such as paraffin wax, and linear fatty alcohols of from 16 to 24 carbons, such as stearyl or behenyl alcohol.

The anhydrous compositions can contain one or more optional ingredients, such as one or more of those selected from those identified below.

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for cosmetic solids or soft solids. Such cosmetic adjuncts can include skin feel improvers, such as talc or finely divided (i.e. high molecular weight) polyethylene, i.e. not a wax, for example Accumist™, in an amount of 1 up to about 10%; a moisturiser, such as glycerol or polyethylene glycol (mol wt 200 to 600), for example in an amount of up to about 5%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A further optional ingredient comprises a preservative, such as ethyl or methyl paraben or BHT (butyl hydroxy toluene) such as in an amount of from 0.01 to 0.1% w/w.

Aerosol compositions desirably additionally comprise a suspending aid, sometimes called a bulking agent which is typically a powdered silica or a layered clay, such as a hectorite, bentonite or montmorillonite. The layered clay is optionally hydrophobically surface treated. The suspending aid often constitutes from 0.5 to 4% by weight of the base aerosol composition (i.e. the composition minus any associated volatile propellant). Aerosol compositions desirably also can contain a swelling aid to assist swelling of the layered clay, often selected in a proportion of from 0.005 to 0.5% by weight of the aerosol base composition and particularly in a weight ratio to the clay of from 1:10 to 1:75. Suitable swelling aids include especially propylene carbonate and triethyl citrate.

The invention compositions can additionally comprise a non-encapsulated fragrance, for example in a weight % of from 0.01 to 4% of the composition, and particularly from 0.1 to 1.5%. The non-encapsulate fragrance is desirably incorporated into the composition in a weight ratio to the shear-sensitive encapsulate in the range of from 5:1 to 1:5. The non-encapsulated fragrance can be created from the same palette of perfume materials described above. The non-encapsulated fragrance can, if desired, be the same as or similar to the encapsulated fragrance, but it is often more attractive if the two fragrances are different, because this minimises the extent to which the nose has become desensitised to perfume. Choice of the various fragrances and the differences between them, such as proportion of top notes, is primarily a matter of aesthetic judgement.

Additionally or alternatively to the non-encapsulated fragrance, if desired the compositions herein can comprise fragrance encapsulated in a water-sensitive shell, such that when a person sweats, the aqueous excretion ruptures the shell, releasing fragrance. Such water-sensitive encapsulates are described for example in EP0303461. Additionally or likewise alternatively, the compositions herein can comprise a cyclic oligosaccharide such as cyclodextrins, including a or β cyclodextrin, each optionally substituted by a methyl or hydroxy-propyl group that associates reversibly with free fragrance. Such materials are described in EP1289484. The composition can contain the water-sensitive fragrance encapsulate and/or cyclic oligosaccharide in an amount of from 0.1% to 4% by weight of the composition.

The weight ratio of shear-sensitive encapsulate to water-sensitive encapsulate and/or cyclic oligosaccharide is often selected in the range of from 5:1 to 1:5.

The invention compositions, be they the full composition for use in contact applicators or the base composition for mixture with a propellant for aerosol compositions desirably are substantially or totally free from water-soluble short chain monohydric alcohols (commonly recognised as up to $C_6$) and especially ethanol. Substantially in this context indicates a proportion of less than 5% and preferably less than 1% by weight of the respective full or base composition.

Herein unless the context demands otherwise, all weights, %s, and other numbers can be qualified by the term "about".

The compositions of the invention may be made by any of the methods known in the art. In preferred methods, the fragrance capsules are incorporated into the composition with gentle mixing; at a rate and power input that does not damage the capsules. It is further preferred that the composition is not subsequently subjected to shear or intensive mixing.

One convenient process sequence for preparing a stick or soft composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the gellants. However, the fragrance oil, be it encapsulated or free, is commonly the last ingredient to be incorporated into the composition, after the antiperspirant active on account of its sensitivity often to elevated temperature. Commonly the resultant structurant solution is allowed to cool to a temperature that is intermediate between that at which the gellants dissolved and the temperature at which it would set, often reaching a temperature in the region of 60 to 90° C.

In some routes, the carrier oils can be mixed together prior to introduction of the gellants and the antiperspirant or deodorant active. In other preparative routes, it is desirable to dissolve all or a fraction of the gellants and especially for amido gellants in a first fraction of the composition, such as a branched aliphatic alcohol, e.g. isostearyl alcohol or octyldodecanol, optionally in conjunction with an alcohol having some water-miscibility and boiling point above the dissolution temperature of the amido gellant in the alcoholic fluid. This enables the remainder of the carrier fluids to avoid being heated to the temperature at which the structurants dissolve or melt. Such a process commonly involves mixing the fractions intensively in for example a "Sonolator"™. In the invention compositions, the fragrance capsules are most desirably introduced after any intensive mixing step. The proportion of the carrier fluids for dissolving the structurants is often from 25 to 50% by weight of the carrier fluids.

In said other preparative routes the particulate material is introduced preferably a second fraction of the carrier oils, for example silicone and/or ester and/or hydrocarbon oils and thereafter, the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature. Cooling may be brought about by nothing more than allowing the container and contents to cool. Cooling may be assisted by blowing ambient or even refrigerated air over the containers and their contents.

Suspension roll-on compositions herein can be made by first charging a mixing vessel equipped with agitation means such as a stirrer or a recycle loop with the oils simultaneously or sequentially, and thereafter charging the vessel with the antiperspirant/deodorant active ingredient, the thickener and any optional ingredient and heating the composition to the extent necessary to dissolve any organic thickener in the oil blend. Thereafter, the resultant fluid composition is discharged into roll-on dispensers through the open top and the ball (or more unusually cylindrical roller) inserted and the cap fitted.

Aerosol products herein comprise a base composition comprising an antiperspirant and/or deodorant active suspended in an oil blend together with the fragrance capsules, suspending agent and optional ingredients that is blended with a propellant, commonly in a weight ratio of blend to propellant of from 1:1 to 1:15, and in many formulations from 1:3 to 1:9. The propellant is commonly either a compressed gas or a material that boils at below ambient temperature, preferably at below 0° C., and especially at below −10° C. Examples of compressed gasses include nitrogen and carbon dioxide. Examples of low boiling point materials include dimethylether, $C_3$ to $C_6$ alkanes, including in particular propane, butanes and isobutane, optionally further containing a fraction of pentane or isopentane, or especially for use in the USA the propellant is selected from hydrofluorocarbons containing from 2 to 4 carbons, at least one hydrogen and 3 to 7 fluoro atoms.

Aerosol products can be made in a conventional manner by first preparing a base composition, charging the composition into the aerosol can, fitting a valve assembly into the mouth of the can, thereby sealing the latter, and thereafter charging the propellant into the can to a desired pressure, and finally fitting an to actuator on or over the valve assembly together.

Having summarised the invention and described it in more detail, together with preferences, specific embodiments will now be described more fully by way of example only.

EXAMPLES

Capsules E1 and E2

The capsules E1 and E2 described herein comprised a shell made from a complex coacervate of gelatin with respectively gum arabic or carboxymethylcellulose, cross-linked with glutaraldehyde. E1 is prepared in accordance with the process of WO2006/056096, but with a higher level of incorporated perfume, and E2 in accordance with the process of U.S. Pat. No. 6,045,835, but again with a higher level of incorporated perfume, and in each instance with conditions controlled to obtain the specific characteristics detailed in Table 1.

TABLE 1

| Characteristic | Capsules E1 | Capsules E2 |
| --- | --- | --- |
| Mean particle size D[4, 3] (1) | 48.4 μm | 50.7 μm |
| Shell thickness (2) (of capsules having diameter from 19 to 38 μm) | 0.3 to 0.65 μm | |
| Shell thickness (2) (of capsules having diameter from 25 to 35 μm) | | 0.25 to 0.6 μm |
| Calculated shell thickness (3) at mean particle size | 1.3 μm | 1.8 μm |
| Ratio of capsule diameter to shell thickness | 30:1 to 48:1 | 23:1 to 36:1 |
| Hysitron hardness (4) | 4.05 MPa | 4.88 MPa |
| Apparent Reduced Elastic Modulus (4) | 24.1 MPa | 27.5 MPa |
| Encapsulated oil (% w/w) | 85 | 80 |
| Encapsulated perfume (% w/w) | 40 | 80 |
| R.I. of capsule | 1.430 | 1.530 |

(1) Mean Particle Size (D[4, 3]) of the capsules was measured following dispersion in cyclopentadimethicone (R.I. 1.397) using a Malvern Mastersizer 2000, with a dispersion module speed of 2100 rpm, a "general purpose" results calculation model, a "normal" calculation sensitivity, and "spherical" selected as the particle shape.
(2) Shell Thickness was measured by SEM on capsules having a particle size within the range indicated. For non-spherical capsules, the thickness was measured at or close to the minimum encapsulate diameter.
(3) The calculated shell thickness assumes that capsules are spherical, with a single core and that the shell and core had the same density.
(4) The Hysitron hardness and Apparent Reduced Elastic Modulus were measured using a Hysitron Tribo-indenter (further details below).

The Hysitron hardness and Apparent Reduced Elastic Modulus of the capsules were measured using the method in the general description. To prepare the capsules for measurement, a drop of a dispersion of the capsules in demineralised water was placed onto a piece of silicon wafer and allowed to dry leaving behind discrete capsules for mechanical analysis. The dried wafer was fitted into a Hysitron Tribo-indenter, and spatially mapped using the optical system of the instrument to identify a perimeter around the sample.

Results are expressed as averages of a minimum of 20 measurements made on capsules with a particle size of D[4, 3]+/−20%.

Examples 1 and 2

In these Examples, the effectiveness across time of adding capsules E1 or E2 to conventional antiperspirant compositions was assessed. Stick and aerosol compositions as indicated in Table 2 were tested. The aerosol base composition was gassed with propellant (base: propellant=13:87 by weight) prior to application.

TABLE 2

| Ingredient | Stick | | | Aerosol Base |
|---|---|---|---|---|
| | % by weight | | | |
| Cyclomethicone | Balance | | | Balance |
| Ester oil | 15.0 | | | |
| Ether Oil | 9.5 | | | 23.1 |
| Dimethiconol | | | | 0.56 |
| Stearyl alcohol | 18.0 | | | |
| Castor wax | 3.5 | | | |
| PE wax | 1.0 | | | |
| Suspending Aid | | | | 3.8 |
| Swelling Aid | | | | 0.1 |
| AZAG | 24.00 | | | |
| AACH | | | | 38.5 |
| AP co-gellant | | | | 3.8 |
| Preservative | 0.05 | | | |
| Fragrance Bm | 1.5 1.5 1.5 | | | |
| Fragrance Cn | 1.2 1.2 1.2 | | | 4.6 4.6 4.6 |
| Capsule E1 | 1.5 | 1.5 | | 4.6 |
| Capsule E2 | 0.7 | 0.7 | | 4.3 |

In the stick compositions with E1 and E2, the encapsulated fragrance content was 0.6% (1.5×0.40) and 0.56% (0.7×0.80), respectively. In the aerosol base compositions with E1 and E2, the encapsulated fragrance content was 1.84%. Each of these figures is significantly lower than the level of free fragrance present.

The effectiveness of the formulations was determined in the following test. 24-26 panelists self-applied approximately 0.3 g example stick product to either the left or right armpit and a control product to the other, with overall left-right randomized balance. The aerosol test product and control product were similarly applied using an approximately 2 second spray. "Test" formulations comprising the added capsules E1 or E2 (containing a floral-green fragrance) were compared with control formulations that contained just a fruity-floral (Bm) or a floral aldehydic (Cn) non-encapsulated fragrance. The effects across time of the added encapsulated fragrances are indicated in Tables 3 and 4.

After application of the antiperspirant formulations, the users put on their normal clothing and the intensity of the odour was assessed by an expert panel at 2 hourly intervals on a scale of perception increasing from 0 to 10. The scores were averaged and that for the control sample deducted from that for the "test" sample. Three scores were measured, namely intensity of the fragrance itself, the intensity detected through the clothing and finally the intensity of any malodour. The results are summarised in Table 3 (for the stick products) and in Table 4 (for the aerosol products).

Interesting, it may be seen that the fragrance intensity difference resulting the added fragrance capsules increases for about 6 to 8 hours, for example, and then falls away somewhat. In contrast, the intensity of non-encapsulated fragrances tends to fall away from the start.

TABLE 3

Stick Results (Example 1)

| | Direct | | Through Clothing | | Malodour | |
|---|---|---|---|---|---|---|
| | Difference in Intensity of E1 test sticks: | | | | | |
| Assessment time (hr.) | E1 + Cn vs. Cn | E1 + Bm vs. Bm | E1 + Cn vs. Cn | E1 + Bm vs. Bm | E1 + Cn vs. Cn | E1 + Bm vs. Bm |
| 0 | 0.89 | 0.92 | 1.04 | 0.72 | n/d | n/d |
| 2 | 1.5 | 0.96 | 1.25 | 0.68 | −0.17 | n/d |
| 4 | 1.63 | 1.28 | 1.79 | 0.98 | −0.17 | n/d |
| 6 | 2.04 | 1.12 | 1.54 | 1.08 | −0.08 | n/d |
| 8 | 1.52 | 1.4 | 1.62 | 0.92 | −0.38 | n/d |
| 10 | 1.64 | 0.92 | 1.50 | 0.68 | −0.46 | n/d |
| 12 | 1.5 | 0.86 | 1.08 | 0.69 | −0.50 | n/d |
| 14 | 1.04 | 0.68 | 0.66 | 0.72 | −0.17 | n/d |

| | Direct | | Through Clothing | | Malodour | |
|---|---|---|---|---|---|---|
| | Difference in Intensity of E2 test sticks: | | | | | |
| Assessment time (Hrs) | E2 + Cn vs. Cn | E2 + Bm vs. Bm | E2 + Cn vs. Cn | E2 + Bm vs. Bm | E2 + Cn vs. Cn | E2 + Bm vs. Bm |
| 0 | 0.09 | 1.31 | 0.71 | 0.81 | n/d | n/d |
| 2 | 2.04 | 1.62 | 1.54 | 1.19 | −0.12 | 0 |
| 4 | 2.41 | 1.69 | 1.71 | 1.84 | −0.2 | −0.08 |
| 6 | 2.16 | 1.54 | 1.54 | 0.89 | −0.42 | −0.13 |
| 8 | 1.96 | 1.54 | 1.63 | 1.84 | −0.46 | −0.27 |
| 10 | 1.90 | 1.57 | 1.58 | 1.88 | −0.39 | −0.35 |
| 12 | 1.58 | 1.54 | 1.08 | 0.81 | −0.50 | −0.39 |
| 14 | 1.37 | 0.93 | 0.91 | 0.77 | −0.37 | −0.39 |

TABLE 4

Aerosol Results (Example 2)

| | Difference in Intensity | | | | | |
|---|---|---|---|---|---|---|
| | Direct | | Through Clothing | | Malodour | |
| Assessment time (Hrs) | E1 + Cn vs. Cn | E2 + Cn vs. Cn | E1 + Cn vs. Cn | E2 + Cn vs. Cn | E1 + Cn vs. Cn | E2 + Cn vs. Cn |
| 0 | 0.93 | 0.25 | 0.24 | 0.31 | n/d | n/d |
| 2 | 1.21 | 1.07 | 0.44 | 0.62 | −0.19 | 0.00 |
| 4 | 1.06 | 0.94 | 0.32 | 0.81 | −0.06 | 0.06 |
| 6 | 0.96 | 1.00 | 0.75 | 1.31 | 0.12 | −0.25 |
| 8 | 0.77 | 1.12 | 0.37 | 1.00 | −0.31 | −0.69 |
| 10 | 0.29 | 0.75 | 0.44 | 0.75 | −0.25 | −0.81 |
| 12 | 0.31 | 0.62 | 0.31 | 0.75 | −0.13 | −0.50 |

From Tables 3 and 4, it is apparent that a greater intensity of the fragrance was perceived from the test samples compared with the control samples throughout the period of the trial, irrespective of whether was assessed through clothing or directly. In addition, when judging the presence of malodour, the panelists consistently generated negative differences, once a long enough period had elapsed for malodour to have been generated, showing that more malodour developed following treatment with the control compositions than developed following treatment with the test compositions. The longevity of this effect is particularly noticeable, sometimes still delivering peak performance at from 8 to 12 hours after application.

Examples 3 and 4

Clinical trials were conducted to demonstrate the benefit in malodour suppression for compositions according to the invention. The formulations employed in Examples 3 and 4 were the same as those employed in Examples 1 and 2, respectively as were the levels of application.

In these Examples, test and control products were applied daily to the underarm of panelists and the panelist carried out normal daily activities until after 5 or 24 hours, when the effectiveness of the fragrance was assessed by trained assessors both before and after gently rubbing the underarms ("shear"). The malodour in this test was assessed on a scale of from 0 to 5. The results from the stick products are shown in Table 5 and the results from the aerosol products in Table 6.

TABLE 5

Stick Results (Example 3)

| Fragrance comparison | After (hr.) | Odour Score Before shear | After shear |
|---|---|---|---|
| Cn + E1 v Cn | 24 | −0.07 | −0.10 |
| Cn + E2 v Cn | 24 | −0.12 | −0.18 |
| Bm + E1 v Bm | 5 | −0.26 | −0.14 |
| Bm + E1 v Bm | 24 | −0.10 | −0.11 |
| Bm + E2 v Bm | 5 | −0.36 | −0.44 |
| Bm + E2 v Bm | 24 | −0.14 | −0.14 |

It is interesting to note some quite large differences even before the additional "shear" applied by the assessors. This indicates that for the stick formulations at least, significant shear-release of the encapsulated fragrance occurs as at matter of normal daily activities.

TABLE 6

Aerosol Results (Example 4)

| Fragrance comparison | After (hr.) | Odour Score Before shear | After shear |
|---|---|---|---|
| Cn + E1 v Cn | 5 | −0.04 | −0.03 |
|  | 24 | −0.01 | −0.10 |
| Cn + E2 v Cn | 5 | −0.10 | −0.17 |
|  | 24 | −0.04 | −0.12 |

The results summarised in Tables 5 and 6 consistently show that assessors judged that the compositions employing the encapsulated fragrances E1 and E2 reduced malodour to a greater extent than the control compositions over an extended period time.

Example 5 and Comparisons A and B

The compositions indicated in Table 7 were prepared by the method described hereinafter. Composition A contained a typical perfume as used commonly used in antiperspirant stick compositions. Composition B additionally contained 0.595% of a single fragrance accord. The third composition (Example 5) contained the same fragrance perfume accord as Composition B, but encapsulated to give capsules as described earlier as E2. The capsules were added at 0.7% w/w/, equating to 0.56% w/w of the single fragrance accord.

TABLE 7

| Ingredient | Comp A | Comp B % by weight | Ex 5 |
|---|---|---|---|
| cyclomethicone | balance | balance | balance |
| Ester oil 1 | 15 | 15 | 15 |
| Ether oil | 9.5 | 9.5 | 9.5 |
| Stearyl Alcohol | 18 | 18 | 18 |
| Ester Wax 1 | 3.5 | 3.5 | 3.5 |
| Hydrocarbon Polymer | 1 | 1 | 1 |
| AZAG | 24 | 24 | 24 |
| Parfum | 1 | 1 | 1 |
| Fragrance accord | — | 0.595 | — |
| Fragrance accord "in E2" | — | — | 0.7 |
| Preservative | 0.05 | 0.05 | 0.05 |
| Perfume Intensity |  |  |  |
| Immediate | 4.7 | 6.2 | 5.8 |
| After Before final rub | 1.1 | 1.6 | 1.2 |
| 7 hrs. After final rub | 1.4 | 1.6 | 3.6 |

The fragrance intensity was tested by the following method.
1. Weighed amounts of each of the compositions was deposited by wiping a freshly cut surface of the stick compositions across separate sheets of plastic film (average weights: 0.80 g, 0.77 g and 0.77 g resp.).
2. Immediately following application, the fragrance intensity for the deposits was assessed by an expert panel of 10 females using a 1 to 10 linescale.
3. The plastic films were stored in an oven at 37° C., being briefly removed after five hours to be rubbed once with a gloved finger, to mimic in-wear rubbing, and then returned to the oven for a further hour.
4. After a total of six hours at 37° C., the plastic sheets were allowed to equilibrate to room temperature for one hour.
5. The fragrance intensity of the sheets were assessed before and after a final single rub with a gloved finger, in the same manner as the immediate assessment.

The average scores of the 10 assessors are shown at the bottom of Table 7. It is noteworthy that the encapsulated fragrance accord retained superior ability to yield increased fragrance, when subjected to rubbing, after an extended period at body temperature of 37° C.

Components of Compositions

Ingredients included in the examples and comparative examples herein described are detailed in Table 8.

TABLE 8

| Ingredient | Name and/or Trade Name | Supplier |
|---|---|---|
| Cyclomethicone [1] | DC 245 | Dow Corning Inc |
| Ester oil 1 [2] | C12-15 alkyl benzoate Finsolv TN | Finetex |
| Ester oil 2 [3] | Isopropyl myristate Estol 1512 | Uniqema |
| Ester Oil 3 | 2-phenylethyl benzoate Finsolv SUN | Finetex |
| Ether Oil | PPG-14-butyl ether/ Fluid AP | Ucon Inc |
| Dimethicone | Dow Corning Fluid 200 (350 cSt) | Dow Corning Inc |
| Branched alcohol [4] | Isostearyl alcohol Prisorine 3515 | Uniqema |
| Dimethiconol in cyclomethicone | DC 1501 | Dow Corning Inc |
| Stearyl alcohol [5] | Lanette C18 | Cognis |
| Ester wax 1 [6] | Castor wax Castorwax MP80 | CasChem Inc |
| Ester wax 2 [7] | Alkyl stearate behenate Kester Wax 82N | Koster Keunen |
| Ester wax 3 | Triglyceride wax Synchrowax HGL-C | Croda Ltd |

TABLE 8-continued

| Ingredient | Name and/or Trade Name | Supplier |
|---|---|---|
| Hydrocarbon wax 1 | Polyethylene Performalene 400 | New Phase Technologies (Baker Petrolite) |
| Hydrocarbon wax 2 | Paraffin wax SP173P | Strahl & Pitsch Inc |
| Hydrocarbon Polymer | Styrene-ethylene/butylene-styrene block copolymer/Kraton G1650E | Kraton Polymers |
| SMGA 1 | N-(2-ethyl hexanoyl)-L-glutamic acid di-n-butylamide GA-01 | Ajinomoto |
| SMGA 2 | N-lauroyl-L-glutamic acid di-n-butylamide GP1 | Ajinomoto |
| SMGA 3 | 12-hydroxystearic acid | CasChem |
| Silicone Elastomer | 10% w/w in cyclomethicone DC9040 | Dow Corning Inc |
| Fumed silica | fumed silica Cab-o-sil | Cabot |
| Layered Clay | treated hectorite/Bentone 38 | Rheox Inc |
| Swelling Aid | Propylene carbonate | |
| ACH | Aluminium chlorohydrate Micro Dry | Reheis Inc |
| AACH | Activated aluminium chlorohydrate A296 | B K Giulini GmbH |
| AZAG | Aluminium zirconium tatrachlorohydrex-Gly Reach 908 | Reheis Inc |
| Polymer AP cogellant | PVM/MA Copolymer Gantraz S95S | International Speciality Products |
| Preservative | Butylhydroxytoluene Tenox BHT | Eastman Chemicals |
| E1 | As described above | |
| E2 | As described above | |
| ES3 | Starch encapsulate | Givaudan Fragrance House |
| Free Fragrance | | |
| Propellant | Propane, butane and isobutane CAP40 | Calor Gas Ltd. |

[1] DC245 can be replaced * by DC246 or DC345 ™.
[2] Finsoln TN can be replaced * by Finsolv TPP ™.
[3] Estol 1512 can be replaced * by Estol 1517 ™.
[4] Prisorine 3515 can be replaced * by Eutanol G16 ™.
[5] Lanette 18 can be replaced partly (up to 50%) by Lanette 16 ™ and/or Lanette 22 ™.
[6] Castorwax MP80 can be replaced * by Castorwax MP90 ™.
[7] Kester Wax 62 can be replaced by Kester Wax 69H.
* Wholly or partly.

Manufacture of Stick Products

The stick products described herein are typically prepared/packaged in the following manner. Stick products are made by filling a dispenser comprising a barrel oval in cross section having a base and an open top covered by a cap, a platform fitting snugly within the barrel at a position intermediate between the base and the top and advancement means for the platform mounted under the base, said means comprising a rotor wheel and an attached threaded spindle engaging a cooperating thread in the platform with a composition summarised in the Table below. The summarised stick compositions are made by the following general method.

The selected oil or oils are charged in the desired weight proportion into a vessel, the desired gellant or mixture of gellants in the desired weight proportion is introduced and the resultant mixture is agitated with an agitator of suitable power or by circulation through a recirculation loop, and heated until a temperature is reached at which the gellant or all the gellants have dissolved in the oils. For waxes that temperature is commonly in the range of from 75 to 90° C. For SMGAs, depending on the particular SMGA, that temperature is often from 90 to 120° C. Thereafter, the mixture is allowed to cool by 5 to 15° C. and the desired weight proportion of particulates other than the encapsulated fragrance (including particularly the antiperspirant active) are introduced with continued agitation. The mixture is cooled or allowed to cool to a temperature of about 5 to 10° C. above the normal setting temperature of the composition (which has been determined in a previous trial). Finally, with gentle agitation, the encapsulated fragrance and any non-encapsulated (free) fragrance are introduced and the still mobile composition is charged into the dispenser.

Stick Formulations

The stick formulations detailed in Table 9 may be prepared in the manner described above.

TABLE 9

| | Example No | | | | | |
|---|---|---|---|---|---|---|
| | 6 | 7 | 8 | 9 | 10 | 11 |
| Ingredient | Parts by weight | | | | | |
| Cyclomethicone | 34.0 | 26.0 | 47.5 | 25.0 | | 37.5 |
| Ester oil 1 | 6.0 | 15.0 | | 17.5 | | 10.0 |
| Ester oil 2 | 6.0 | | | | | |
| Ester Oil 3 | | | | | 53.15 | |
| Ether Oil | 10.0 | 9.5 | 15.0 | 15.5 | | 5.0 |
| Dimethicone | | | 5.0 | 1.0 | | |
| Branched alcohol | | | | | 11.45 | 14.0 |
| Stearyl alcohol | 15.5 | 18.0 | | | | |
| Ester wax 1 | 4.0 | 3.5 | | | | |
| Ester wax 2 | | | 10.0 | | | |
| Hydrocarbon wax 1 | | 1.0 | | 8.0 | | |
| Hydrocarbon wax 2 | | | | 6.0 | | |
| Hydrocarbon Polymer | | | | | 5.9 | |
| SMGA 1 | | | | | 2.5 | |
| SMGA 2 | | | | 2.5 | | 2.5 |
| SMGA 3 | | | | | | 7.0 |
| ACH | 24.0 | | | | | |
| AACH | | | 20.0 | | | 22.0 |
| AZAG | | 24.0 | | 24.5 | 22.5 | |
| E1 | | 1.5 | 1.5 | | | 2.0 |
| E2 | 0.5 | | | 2.0 | 1.0 | |
| ES3 | | | | 0.5 | | |
| Free Fragrance | | 1.5 | 1.0 | | 1.5 | |

The aerosol products described herein are typically prepared/packaged in the following manner. All of the ingredients of the base composition are blending in a vessel at ambient temperature until an homogenous mixture is obtained. Then the base composition is charged into a preformed aluminium can, a valve cup supporting a valve from which depends a dip tube is crimped into place, and propellant is charged into the can through the valve. Thereafter, an actuator is placed above the valve stem extending upwards from the valve.

The soft solid products described herein are typically prepared/packaged in the following manner. The soft solid formulations are charged into a dispenser having its top covered by a dome with narrow apertures. Those made with a wax gellant are made by a similar process to that of the stick formulations, the amount being insufficient to produce a hard stick. Those made using a silica thickening agent involve stirring a suspension of all the ingredients in a vessel at a temperature in the range of 25 to 50° C. until an homogeneous suspension is obtained, and thereafter top filling it into the dispenser and placing the dome in the mouth.

The further examples indicated below may be prepared in the manner described herein.

In Example 14, a roll-on formulation is made by a similar method to Example 13, but employing less thickener.

In Example 15, the roll-on formulation of Example 14 is absorbed into a non-woven applicator cloth.

|  | Example No | | | | | |
|---|---|---|---|---|---|---|
| Ingredient | 12 | 13 | 14 | 16 | 17 | 18 |
|  | Parts by weight | | | | | |
| Cyclomethicone | 32.5 | 32.0 | 54.5 | 7.0 | 2.79 | 5.6 |
| Ester oil 1 | 14.0 | 10.0 | 15.0 | 5.0 |  | 1.0 |
| Ester oil 2 | 7.5 |  |  | 2.3 |  |  |
| Ether Oil |  | 5.0 | 10.0 |  | 3.0 |  |
| Dimethicone | 8.0 | 7.0 | 2.0 | 3.0 |  |  |
| Ester wax 3 | 3.25 |  |  |  |  |  |
| Hydrocarbon wax 2 | 3.25 |  |  |  |  |  |
| Silicone elastomer | 4.0 |  |  |  |  |  |
| Fumed silica |  | 5.0 | 1.5 | 0.4 |  |  |
| Layered Clay |  |  |  | 1.25 | 0.5 | 0.5 |
| Swelling Aid |  |  |  | 0.05 | 0.01 |  |
| ACH |  |  | 15.0 | 10.0 |  |  |
| AACH |  | 12.0 |  |  | 5.0 | 5.0 |
| AZAG | 25.0 | 12.0 |  |  |  |  |
| Propellant |  |  |  | 70.0 | 87.0 | 87.0 |
| E1 | 1.5 |  | 1.0 | 0.5 | 0.6 |  |
| E2 |  | 1.5 |  |  |  | 0.3 |
| ES3 | 0.5 | 0.5 |  |  | 0.1 |  |
| Free Fragrance | 0.5 |  | 1.0 | 0.5 | 1.0 | 0.6 |

The invention claimed is:

1. An anhydrous aerosol antiperspirant composition comprising propellant; particulate antiperspirant active; capsules comprising a shear-sensitive shell which encapsulates perfume; and a carrier for the particulate antiperspirant active and capsules; wherein the capsules have a shell of cross-linked gelatin coacervate having a thickness of from 0.25 to 9 μm and providing from 10 to 40% by weight of the capsules, a volume average particle diameter of from 25 to 70 μm, a ratio of shell thickness to the average particle diameter in the range of from 1:5 to 1:120, and a Hysitron hardness in the range of from 1.5 MPa to 50 MPa, wherein said capsules are present in an amount of up to 5% by weight of the composition.

2. A composition according to claim 1 in which the cross-linked shell is obtained by contacting gelatin with either gum arabic or a charged carboxymethyl cellulose at a pH of below 5 to form a gelatin coacervate that is subsequently cross-linked.

3. A composition according to claim 1 in which the coacervate is cross-linked with glutaraldehyde.

4. A composition according to claim 1 in which the capsules have a particle size D[4,3] in the range of from 40 to 60 μm.

5. A composition according to claim 1 in which the capsules have a measured shell thickness in the range of 0.25 μm up to 2.5 μm.

6. A composition according to claim 1 in which the capsules have an average measured shell thickness in the range of from 0.3 to 0.8 μm.

7. A composition according to claim 1 in which the capsules have an average particle size to shell thickness ratio in the range of from 40:1 to 80:1.

8. A composition according to claim 1 in which the capsules have shells providing from 12 to 25% by weight of the capsules.

9. A composition according to claim 1 in which the capsules have a Hysitron hardness in the range of from 2.5 to 4 MPa.

10. A composition according to claim 1 in which the capsules have an apparent reduced elastic modulus in the range of from 10 to 3 MPa.

11. A composition according to claim 1 in which the capsules have a water content of less than 5%.

12. A composition according to claim 1 which contains from 0.1 to 4% by weight of the capsules.

13. A composition according to claim 1 which additionally contains non-encapsulated fragrance.

14. A composition according to claim 1 in which the composition comprises from 30 to 70% w/w volatile silicone oil and from 20 to 40% w/w ester oil and/or ether oil.

15. A composition according to claim 14 in which at least 90% w/w of the volatile silicone oil is cyclomethicone having from 5 to 6 silicon atoms.

16. A composition according to claim 14 in which the ester oil is an alkyl benzoate and optionally a triglyceride oil of an unsaturated $C_{18}$ fatty acid.

17. A composition according to claim 1 in which the particulate antiperspirant active is selected from aluminium chlorohydrates, optionally complexed with glycine.

18. A composition according to claim 1 which is free from ethanol.

19. A composition according to claim 1 which additionally contains a water-sensitive encapsulated fragrance.

* * * * *